United States Patent [19]

Kirkpatrick

[11] 4,220,790
[45] Sep. 2, 1980

[54] 1-N,N-DIMETHYLCARBAMYL-3-TERT.BU-TYL-5-METHYLTHIO-1,2,4-TRIAZOLE

[75] Inventor: Joel L. Kirkpatrick, Overland Park, Kans.

[73] Assignee: Gulf Oil Corporation, Pittsburgh, Pa.

[21] Appl. No.: 842,760

[22] Filed: Oct. 17, 1977

Related U.S. Application Data

[63] Continuation-in-part of Ser. No. 662,171, Mar. 1, 1976, Pat. No. 4,066,774.

[51] Int. Cl.³ .................... A01N 47/38; C07D 249/12
[52] U.S. Cl. ..................................... 548/265; 424/269
[58] Field of Search ..................... 260/308 R; 548/265

[56] References Cited

U.S. PATENT DOCUMENTS

| 3,308,131 | 5/1967 | McKusick | 260/308 R |
| 3,952,001 | 4/1976 | Brookes et al. | 260/308 R |
| 4,054,664 | 10/1977 | Watkins et al. | 424/269 |

Primary Examiner—Alton D. Rollins
Attorney, Agent, or Firm—Carl A. Cline

[57] ABSTRACT

Insects of the orders Coleoptera and Orthoptera and corn rootworms in particular are selectively killed in the presence of living plants by applying to the locus of the insects an effective amount of 1-N,N-dimethylcarbamyl-3-tert.butyl-5-methylthio-1,2,4-triazole.

1 Claim, No Drawings

1-N,N-DIMETHYLCARBAMYL-3-TERT.BUTYL-5-METHYLTHIO-1,2,4-TRIAZOLE

This application is a continuation-in-part of copending U.S. Ser. No. 662,171 filed Mar. 1, 1976, now U.S. Pat. No. 4,066,774.

DESCRIPTION OF THE INVENTION a. BACKGROUND OF THE INVENTION

U.S. Pat. No. 3,308,131 discloses a broad class of compounds which are said to be useful as insecticides. Toxicity to mites and aphids is mentioned specifically and in fact it is known that some degree of aphicidal activity is common to most of the specifically disclosed compounds of the class. Miticidal activity of the compounds of the disclosed class is less common and generally of a low order. None of the specifically disclosed compounds in the patent appears to possess adequate efficacy against soil-borne insects combined with sufficiently low mammalian toxicity to meet present day requirements for control of pests such as corn rootworm. Many of the more insecticidal compounds within the disclosed class are highly toxic to mammals (oral $LD_{50}$ values below 5 mg./kg. on laboratory rats).

I have discovered, however, that the compound having the structural formula

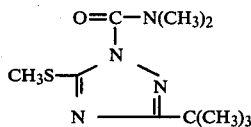

has outstanding properties that are in some aspects inconsistent with the general characteristics of the disclosed class of compounds. Aside from aphicidal activity, this compound is effective against insects of the orders Coleoptera and Orthoptera. It is particularly useful in combating the destructive larvae of these insects, including soil-borne pests, in the presence of growing plants. The high degree of efficacy and broad spectrum of insecticidal activity is accompanied by an absence of miticidal activity and an oral $LD_{50}$ on rats of 15 mg./kg.

b. SUMMARY OF THE INVENTION

Briefly, I have discovered that insects of the orders Coleoptera and Orthoptera and particularly corn rootworms may be killed in the presence of living plants by applying to the locus of the insects an effective amount of the compound having the structural formula

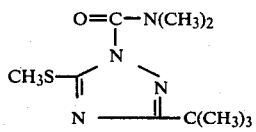

The efficacy of this compound as an insecticide is such that application to the general area or zone (locus) in which the insects live in either larvae or adult forms is sufficient. It is not necessary to apply the insecticide directly to the insects.

This discovery is disclosed in the aforementioned U.S. Ser. No. 662,171.

c. DETAILED DESCRIPTION

The insecticide is conveniently prepared on a laboratory scale by means of the procedures described below.

Preparation of 3-tert.butyl-4H—1,2,4-triazolin-5-thione

To a suspension of 50 g (0.55 mol) of thiosemicarbazide and 43 g (0.05 mol) of pyridine in 300 ml of dioxane was added 42.6 g (0.6 mol) of pivalyl chloride, with cooling. The reaction was stirred at room temperature for 72 hours, then poured into water. The resulting solid was collected, washed with water and dried. The unpurified pivalyl thiosemicarbazide was heated at reflux temperature in 300 ml of 10% sodium hydroxide solution for 3 hours. After cooling, the pH was adjusted to 4 with hydrochloric acid and the product collected, washed with water and dried to give 43.8 g, m.p. 200°–203° C. Recrystallization from methanol chloroform gave a sample, m.p. 203°–205° C.

Preparation of 3-tert.butyl-5-methylthio-4H-1,2,4-triazole

To a suspension of 40 g (0.254 mol) of 3-tert.butyl-4H-1,2,4-triazolin-5-thione in 300 ml of ethanol, was added 40 g (0.28 mol) of methyliodide. After stirring at room temperature for 16 hrs., the reaction was heated at reflux for two hrs., then was concentrated to near dryness on the rotary evaporator. Water was added to dissolve the resulting solids and the solution was taken to pH 9 with dilute $NH_4OH$. The product precipitated and was collected, giving 32.3 g, m.p. 191°–194° C.

Preparation of 1-Dimethylcarbamyl-3-tert.butyl-5-methylthio-1,2,4-1H-triazole

To a solution of 5.0 g (0.029 m) of 3-tert.butyl-5-methylthio-1,2,4-4H-triazole in toluene (100 ml) was added 50 ml of a toluene solution of phosgene (12%) and the reaction was heated to reflux for 2 hrs. After cooling, an excess of aqueous dimethyl amine was added and, after stirring at room temperature for 1 hr. the organic phase was washed with dilute hydrochloric acid, then with water and was then dried over anhydrous sodium sulfate. The toluene was evaporated to near dryness at reduced pressure and the residue was crystallized from hexane. Filtration gave 6.1 g (87%) of 1-dimethylcarbamyl-3-tert.butyl-5-methylthio-1,2,4-1H-triazole, MP 51°–53° C. Spectral properties agree with the structure as represented above:

IR(Nujol) 5.88μ

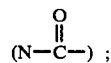

NMR (CDCl₃) (δ1.3(S,9H,t-butyl), 2.6(S,3H,—S—CH₃), δ3.13(S,6H,—N(CH₃)₂).

Use of the Insecticide

Use of the new insecticide is illustrated by means of controlled tests providing a measure of efficacy on various species, according to procedures described below.

Method for Mites, Aphids, Bean Beetles and Army Worms

Three 5 oz. paper cups containing Henderson dwarf lima bean plants and one 5 oz. paper cup containing Orange Gem nasturtiums, all growing in vermiculite, are placed on a turntable and sprayed to thorough wetness with 25 ml of a solution of the candidate chemical at the appropriate concentration. Nasturtiums were already infested with 50–100 bean aphids (BA). A bean plant in one paper cup was already infested with 50–100 two-spotted mites (TSM). Leaves from the two remaining bean plants are removed following spraying and placed in disposable petri dishes with 5 southern armyworm (SA) larvae in one petri dish, and 5 Mexican bean beetle (MBB) larvae in the other petri dish. The rating is done approximately 48 hours after spraying as follows:

| BA | TSM |
|---|---|
| 0 = none dead | 0 = no dead adults |
| 1 = 1–25% dead | 1 = 1–25% dead adults |
| 2 = 26–50% dead | 2 = 26–50% dead adults |
| 3 = 51=75% dead | 3 = 51–75% dead adults |
| 4 = 76–100% dead | 4 = 76–99% dead adults |
| 5 = 100% dead | 5 = 100% dead adults |

| MBB | SA |
|---|---|
| 0 = no larvae dead | 0 = no larvae dead |
| 1 = 1–25% larvae dead | 1 = 1–25% larvae dead |
| 2 = 26–50% larvae dead | 2 = 26–50% larvae dead |
| 3 = 51–75% larvae dead | 3 = 51–75% larvae dead |
| 4 = 76–99% larvae dead | 4 = 76–99% larvae dead |
| 5 = 100% larvae dead | 5 = 100% larvae dead |

Method for Southern Corn Rootworm (SCR)

Three 5 oz. paper cups planted each with one kernel of DeKalb XL-361 corn are treated two days after planting with 10 ml of a 125 ppm solution of the candidate compound. Compounds with high efficacy are tested at lower concentrations. The experiment is a 4×5 factorial in a randomized complete block design with three replications. The tests are evaluated nine days after treatment. The roots are inspected under a dissecting microscope and rated as follows:

| SCR Rating | % Root Feeding Damage |
|---|---|
| 5 | 0 |
| 4 | 1–25 |
| 3 | 26–50 |
| 2 | 51–75 |
| 1 | 76–99 |
| 0 | 100 |

So as to obtain more meaningful results, all tests are performed at the same time of day, whenever possible, usually in the forenoon. Temperature, illumination and humidity are the same in all tests. Atmospheric pressure is not controlled.

Results obtained with the novel insecticide of this invention at various concentrations of active chemical are tabulated below. The ratings given are for averages of three or more replicates. The oral lethal dose for 50 percent kill of laboratory rats is also recorded in the table. In conducting the toxicity tests on rats, 0.01 g of active chemical per ml in corn oil is employed as an additive to the diet of the animals.

Insecticidal Use of
1-N,N-Dimethylcarbamyl-3-tert.butyl-5-methylthio-1,2,4-triazole

| Conc. ppm | Mexican bean beetle | Southern Army-worm | Bean A-phid | Two-Spotted Mites | Corn Root-worm | Remarks |
|---|---|---|---|---|---|---|
| 500 | 5 | 1 | 5 | 0 | | |
| 250 | 5 | | 5 | | | |
| 125 | 5 | | 5 | | | Oral |
| 100 | | | | | 5 | $LD_{50}>$ |
| 62 | 5 | | 5 | | | 15 mg/kg |
| | 5 | | | | | |
| 50 | | | | | 5 | |
| 31 | 5 | | 5 | | | |
| | 5 | | 5 | | | |
| 25 | | | | | 5 | |
| 15 | 1 | | 5 | | | |
| | 4 | | 5 | | | |
| 12 | | | | | 5 | |
| 8 | 3 | | 5 | | | |
| 6 | | | | | 3.3 | |
| 4 | 0 | | 3 | | | |
| 3 | | | | | 3 | |
| 2 | | | 1 | | | |

The unique characteristics of the insecticide of this patent become more apparent when the compound is compared with other compounds which are specifically exemplified or lie within the scope of the disclosure of U.S. Pat. No. 3,308,131. Following are tabulated data obtained from tests made according to the procedures disclosed above, in which the insecticide of this invention is compared with several of these closely related compounds. All of the compounds were tested first on mites, aphids, bean beetles and armyworms and only those which exhibited substantial insecticidal activity were tested on corn rootworms.

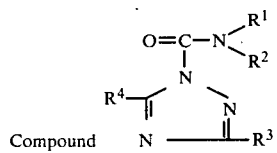

| Compound | Species | Results of Insecticide Tests Conc'n. (ppm) | | | | | | | | |
|---|---|---|---|---|---|---|---|---|---|---|
| | | 500 | 250 | 125 100 | 62 50 | 31 25 | 15 12 | 8 6 | 4 3 | 2 |
| (U.S.Ser.No. 842,760) | | | | | | | | | | |
| $R^1$ methyl | MBB | 5 | 5 | 5 | 5 5 | 5 5 | 1 4 | 3 | 0 | |
| $R^2$ methyl | SA | No test | | | | | | | | |
| | BA | 5 | 5 | 5 | 5 | 5 5 | 5 5 | 5 | 3 | 1 |
| $R^3$ tert.butyl | TSM | 0 | | | | | | | | |
| $R^4$ CH$_3$S— | SCR | | | 5 | 5 | 5 | 5 | 3.3 | 3.0 | |
| U.S. Pat. No. 3,308,131 | MBB | 5 | 5 | 3 | 0 | 0 | 0 | | | |
| (Example X) | SA | 0 | | | | | | | | |
| $R^1$ methyl | BA | 5 | 5 | 5 | 5 5 | 5 5 | 2 | 0 | 0 | |
| $R^2$ methyl | TSM | 0 | | | | | | | | |

-continued

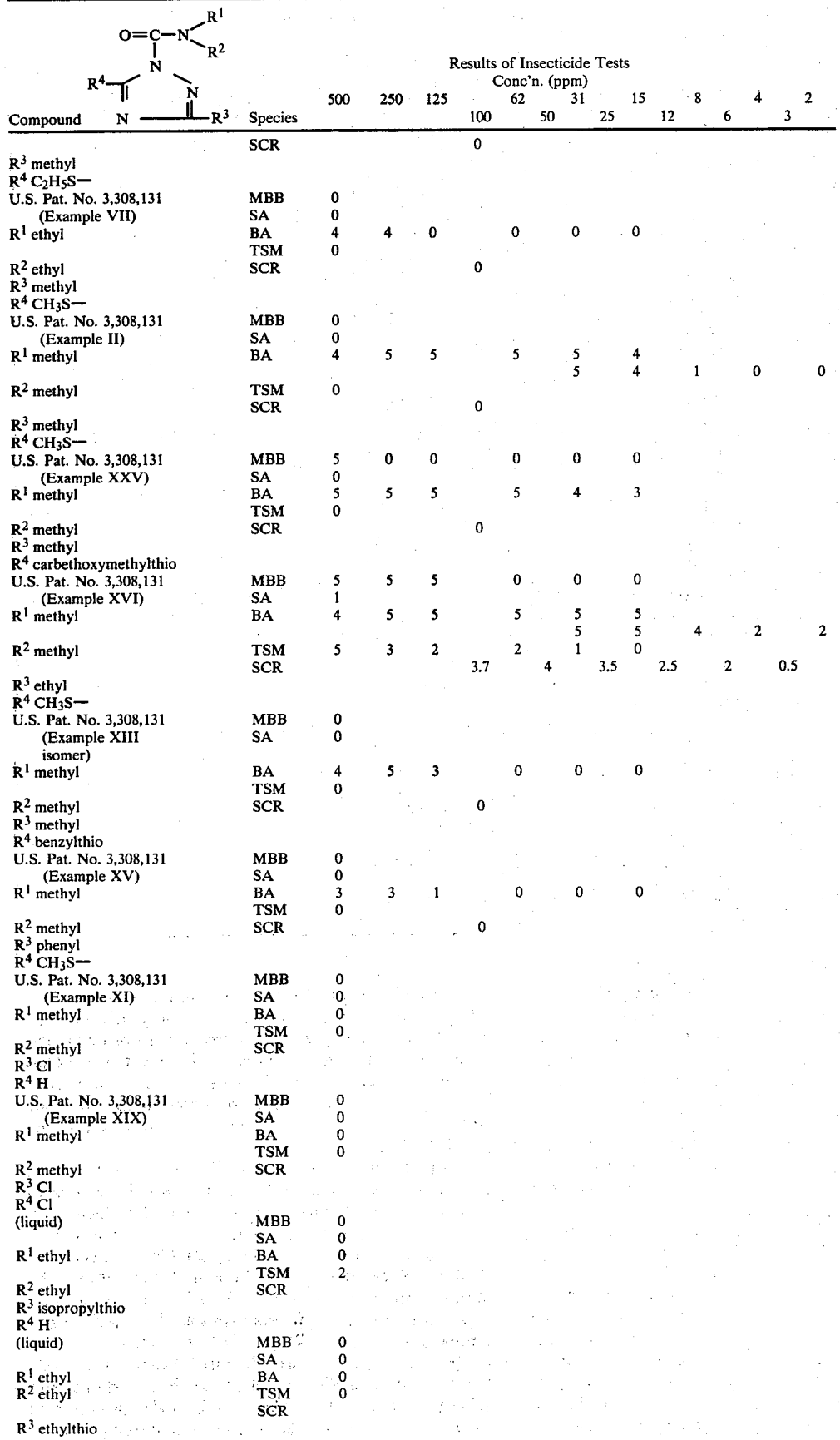

| Compound | Species | 500 | 250 | 125 | 100 | 62 | 50 | 31 | 25 | 15 | 12 | 8 | 6 | 4 | 3 | 2 |
|---|---|---|---|---|---|---|---|---|---|---|---|---|---|---|---|---|
| | SCR | | | | 0 | | | | | | | | | | | |
| R³ methyl | | | | | | | | | | | | | | | | |
| R⁴ C₂H₅S— | | | | | | | | | | | | | | | | |
| U.S. Pat. No. 3,308,131 | MBB | 0 | | | | | | | | | | | | | | |
| (Example VII) | SA | 0 | | | | | | | | | | | | | | |
| R¹ ethyl | BA | 4 | 4 | 0 | | 0 | | 0 | | 0 | | | | | | |
| | TSM | 0 | | | | | | | | | | | | | | |
| R² ethyl | SCR | | | | 0 | | | | | | | | | | | |
| R³ methyl | | | | | | | | | | | | | | | | |
| R⁴ CH₃S— | | | | | | | | | | | | | | | | |
| U.S. Pat. No. 3,308,131 | MBB | 0 | | | | | | | | | | | | | | |
| (Example II) | SA | 0 | | | | | | | | | | | | | | |
| R¹ methyl | BA | 4 | 5 | 5 | | 5 | | 5 | | 4 | | | | | | |
| | | | | | | | | | | 5 | | 4 | | 1 | 0 | 0 |
| R² methyl | TSM | 0 | | | | | | | | | | | | | | |
| | SCR | | | | 0 | | | | | | | | | | | |
| R³ methyl | | | | | | | | | | | | | | | | |
| R⁴ CH₃S— | | | | | | | | | | | | | | | | |
| U.S. Pat. No. 3,308,131 | MBB | 5 | 0 | 0 | | 0 | | 0 | | 0 | | | | | | |
| (Example XXV) | SA | 0 | | | | | | | | | | | | | | |
| R¹ methyl | BA | 5 | 5 | 5 | | 5 | | 4 | | 3 | | | | | | |
| | TSM | 0 | | | | | | | | | | | | | | |
| R² methyl | SCR | | | | 0 | | | | | | | | | | | |
| R³ methyl | | | | | | | | | | | | | | | | |
| R⁴ carbethoxymethylthio | | | | | | | | | | | | | | | | |
| U.S. Pat. No. 3,308,131 | MBB | 5 | 5 | 5 | | 0 | | 0 | | 0 | | | | | | |
| (Example XVI) | SA | 1 | | | | | | | | | | | | | | |
| R¹ methyl | BA | 4 | 5 | 5 | | 5 | | 5 | | 5 | | | | | | |
| | | | | | | | | | | 5 | | 5 | | 4 | 2 | 2 |
| R² methyl | TSM | 5 | 3 | 2 | | 2 | | 1 | | 0 | | | | | | |
| | SCR | | | | 3.7 | | 4 | | 3.5 | | 2.5 | | 2 | | 0.5 | |
| R³ ethyl | | | | | | | | | | | | | | | | |
| R⁴ CH₃S— | | | | | | | | | | | | | | | | |
| U.S. Pat. No. 3,308,131 | MBB | 0 | | | | | | | | | | | | | | |
| (Example XIII isomer) | SA | 0 | | | | | | | | | | | | | | |
| R¹ methyl | BA | 4 | 5 | 3 | | 0 | | 0 | | 0 | | | | | | |
| | TSM | 0 | | | | | | | | | | | | | | |
| R² methyl | SCR | | | | 0 | | | | | | | | | | | |
| R³ methyl | | | | | | | | | | | | | | | | |
| R⁴ benzylthio | | | | | | | | | | | | | | | | |
| U.S. Pat. No. 3,308,131 | MBB | 0 | | | | | | | | | | | | | | |
| (Example XV) | SA | 0 | | | | | | | | | | | | | | |
| R¹ methyl | BA | 3 | 3 | 1 | | 0 | | 0 | | 0 | | | | | | |
| | TSM | 0 | | | | | | | | | | | | | | |
| R² methyl | SCR | | | | 0 | | | | | | | | | | | |
| R³ phenyl | | | | | | | | | | | | | | | | |
| R⁴ CH₃S— | | | | | | | | | | | | | | | | |
| U.S. Pat. No. 3,308,131 | MBB | 0 | | | | | | | | | | | | | | |
| (Example XI) | SA | 0 | | | | | | | | | | | | | | |
| R¹ methyl | BA | 0 | | | | | | | | | | | | | | |
| | TSM | 0 | | | | | | | | | | | | | | |
| R² methyl | SCR | | | | | | | | | | | | | | | |
| R³ Cl | | | | | | | | | | | | | | | | |
| R⁴ H | | | | | | | | | | | | | | | | |
| U.S. Pat. No. 3,308,131 | MBB | 0 | | | | | | | | | | | | | | |
| (Example XIX) | SA | 0 | | | | | | | | | | | | | | |
| R¹ methyl | BA | 0 | | | | | | | | | | | | | | |
| | TSM | 0 | | | | | | | | | | | | | | |
| R² methyl | SCR | | | | | | | | | | | | | | | |
| R³ Cl | | | | | | | | | | | | | | | | |
| R⁴ Cl | | | | | | | | | | | | | | | | |
| (liquid) | MBB | 0 | | | | | | | | | | | | | | |
| | SA | 0 | | | | | | | | | | | | | | |
| R¹ ethyl | BA | 0 | | | | | | | | | | | | | | |
| | TSM | 2 | | | | | | | | | | | | | | |
| R² ethyl | SCR | | | | | | | | | | | | | | | |
| R³ isopropylthio | | | | | | | | | | | | | | | | |
| R⁴ H | | | | | | | | | | | | | | | | |
| (liquid) | MBB | 0 | | | | | | | | | | | | | | |
| | SA | 0 | | | | | | | | | | | | | | |
| R¹ ethyl | BA | 0 | | | | | | | | | | | | | | |
| R² ethyl | TSM | 0 | | | | | | | | | | | | | | |
| | SCR | | | | | | | | | | | | | | | |
| R³ ethylthio | | | | | | | | | | | | | | | | |

-continued

Structure:
$$O=C-N\begin{smallmatrix}R^1\\R^2\end{smallmatrix}$$
with $R^4$ and $R^3$ attached to the ring nitrogens.

| Compound | Species | 500 | 250 | 125 | 100 | 62 | 50 | 31 | 25 | 15 | 12 | 8 | 6 | 4 | 3 | 2 |
|---|---|---|---|---|---|---|---|---|---|---|---|---|---|---|---|---|
| $R^4$ methyl (British Patent 1,316,280) | MBB | 0 | | | | | | | | | | | | | | |
| | SA | 0 | | | | | | | | | | | | | | |
| $R^1$ ethyl | BA | 4 | 0 | 0 | | 0 | | 0 | | 0 | | | | | | |
| | TSM | 0 | | | | | | | | | | | | | | |
| $R^2$ ethyl | SCR | | | | 0 | | | | | | | | | | | |
| $R^3$ 2-methylpropylthio | | | | | | | | | | | | | | | | |
| $R^4$ H (liquid) | MBB | 0 | | | | | | | | | | | | | | |
| | SA | 0 | | | | | | | | | | | | | | |
| $R^1$ ethyl | BA | 4 | 0 | 0 | | 0 | | 0 | | 0 | | | | | | |
| | TSM | 0 | | | | | | | | | | | | | | |
| $R^2$ ethyl | SCR | | | | 0 | | | | | | | | | | | |
| $R^3$ 2-methylpropylthio | | | | | | | | | | | | | | | | |
| $R^4$ methyl (liquid) | MBB | 0 | | | | | | | | | | | | | | |
| | SA | 0 | | | | | | | | | | | | | | |
| $R^1$ methyl | BA | 4 | 4 | 4 | | 2 | | 1 | | 0 | | | | | | |
| | TSM | 0 | | | | | | | | | | | | | | |
| $R^2$ methyl | SCR | | | | 0 | | | | | | | | | | | |
| $R^3$ benzyl | | | | | | | | | | | | | | | | |
| $R^4$ CH$_3$S— (liquid) | MBB | 0 | | | | | | | | | | | | | | |
| $R^1$ plus $R^2$ pentamethylene | SA | 0 | | | | | | | | | | | | | | |
| $R^3$ tert.butyl | BA | 0 | | | | | | | | | | | | | | |
| | TSM | 0 | | | | | | | | | | | | | | |
| | SCR | | | | | | | | | | | | | | | |
| $R^4$ benzylthio (m.p. 78°–80° C.) | MBB | 0 | | | | | | | | | | | | | | |
| | SA | 0 | | | | | | | | | | | | | | |
| $R^1$ ethyl | BA | 0 | | | | | | | | | | | | | | |
| $R^2$ ethyl | TSM | 0 | | | | | | | | | | | | | | |
| | SCR | | | | | | | | | | | | | | | |
| $R^3$ tert.butyl | | | | | | | | | | | | | | | | |
| $R^4$ benzylthio (m.p. 79°–80° C.) | MBB | 0 | | | | | | | | | | | | | | |
| | SA | 0 | | | | | | | | | | | | | | |
| $R^1$ ethyl | BA | 0 | | | | | | | | | | | | | | |
| $R^2$ ethyl | TSM | 0 | | | | | | | | | | | | | | |
| $R^3$ p-methylbenzylthio | SCR | | | | | | | | | | | | | | | |
| $R^4$ methyl (m.p. 98°–99° C.) | MBB | 0 | | | | | | | | | | | | | | |
| | SA | 0 | | | | | | | | | | | | | | |
| $R^1$ plus $R^2$ pentamethylene | BA | 0 | | | | | | | | | | | | | | |
| $R^3$ p-methylbenzylthio | TSM | 0 | | | | | | | | | | | | | | |
| $R^4$ methyl | SCR | | | | | | | | | | | | | | | |

Upon examination of the foregoing tabulated data, it will be seen that of the nineteen compounds in the comparative tests, only the compound of this invention and the compound of Example XVI of the patent displayed toxicity to corn rootworm. The compound of Example XVI obviously has no substantial utility as a corn rootworm insecticide because it failed to give a total kill at any concentration.

Corn rootworm infestations present a particularly difficult problem because the insecticide is put in the soil at planting time but the corn rootworms do not become active until about six weeks later. During this period of time in the soil the insecticide concentration diminishes as a result of leaching and the action of oxygen and soil microbes, so that it is difficult to maintain sufficient concentration to kill the rootworms. Very few insecticides are capable of a sufficiently lasting residual effect so as to possess substantial utility for corn rootworm control. Less than a half dozen compounds enjoy substantial commercial success for this purpose. Of these compounds, carbofuran has proved to be the most consistently effective and commercially successful. Carbofuran was therefore selected as a standard for comparison of his compound and closely related compounds for corn rootworm control under corn growing conditions. The organism used in these tests were Diabrotica undecimpunctata howardi, the Southern corn rootworm. The following method was employed in the tests:

METHOD

Two parallel rows of corn (Pioneer 385 g×526 g untreated) were planted 2" apart down the center of Mirro No. C8509 aluminum bread pans, 5 kernels corn per row in greenhouse potting soil. The dimensions of the bread pans are 9⅝"×5½"×2¾" and lack holes in the bottoms of the pans. Each kernel of corn at time of germination was infested with 3-day-old SCR eggs, approximately 50 eggs per kernel. Test pans were treated by drenching 200 mls of test solution (Triton X-100, water and the test chemical dissolved in 5 mls acetone) on the surface of the soil in the bread pan. The schedule for treating, planting corn, and infesting with corn rootworm eggs were varied to test aging characteristics of the compounds in soil. The test pans were watered daily and held at 80° F. and 50% R.H. until rated. Root damage rating was done by the following rating sequence:

| Rating | % Root Damage Rating |
|---|---|
| 0 | 100 |
| 1 | 76-99 |
| 2 | 50-75 |
| 3 | 26-50 |
| 4 | 1-25 |
| 5 | 0 |

The chemical compound which were tested were those of the structural formula

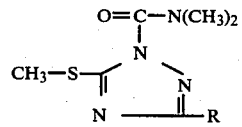

in which R represents tert.butyl, methyl, ethyl, propyl, butyl and isobutyl.

The comparison standard was carbofuran (2,3-dihydro-2,2-dimethyl-7-benzofuranyl methylcarbamate).

The tests were conducted during the months of July and August according to the time schedule as set forth below:

| Test schedule | | | | | Days Interval Between | |
|---|---|---|---|---|---|---|
| Test No. | Rate (lbs/A) | Treated | Date Planted & Infested | Date Rate | Treatment & Infestation | Treatment & Rating |
| 1 | 10.0 | 7-1 | 7-1 | 7-11 | 0 | 11 |
| 2 | 10.0 | 7-1 | 8-1 | 8-10 | 31 | 41 |
| 3 | 1.0 | 7-18 | 7-18 | 7-29 | 0 | 11 |
| 4 | 1.0 | 7-15 | 8-1 | 8-10 | 17 | 26 |
| 5 | 1.0 | 7-1 | 8-1 | 8-10 | 31 | 41 |

The results obtained in the tests are as follows:

Compounds of the formula

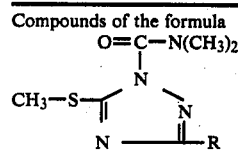

| | AVERAGE ROOT DAMAGE RATINGS | | | | |
|---|---|---|---|---|---|
| Test No: | 1 | 2 | 3 | 4 | 5 |
| Rate: | 10.0 lb/A | 10.0 lb/A | 1.0 lb/A | 1.0 lb/A | 1.0 lb/A |
| Aged: | 11 Days | 41 Days | 11 Days | 26 Days | 41 Days |
| R' = tert.butyl | 5.0 | 4.3 | 4.5 | 4.1 | 4.6 |
| methyl | 2.7 | 0 | 0 | 0.1 | 0.5 |
| ethyl | 4.3 | 3.0 | 0 | 1.1 | 1.0 |
| propyl | 4.4 | 3.1 | 0.3 | 1.8 | 2.3 |
| butyl | 4.4 | 3.6 | 0 | 0.4 | 0.5 |
| isobutyl | 4.8 | 3.6 | 0.6 | 0.3 | 2.3 |
| Carbofuran | 4.8 | 4.1 | 4.3 | 3.8 | 4.7 |
| Infested Checks | 0 | 0 | 0 | 0 | 0 |
| Uninfested Checks | 5.0 | 5.0 | 5.0 | 5.0 | 5.0 |

1 Average rating of 10 individually rated plants

It will be seen from the examination of the foregoing test results that only the compound of this invention possesses efficacy of long duration, comparable to the commercial insecticide which is employed as a comparison standard.

It will be realized by workers in the art that the efficacy of the insecticide at low concentration levels makes it advisable to combine the compound with an inert carrier, according to conventional practice. In this way the compound may be distributed more uniformly at desired concentration levels. Water is the most convenient inert carrier in many situations and it is conventional practice to use commercial emulsifiers and dispersing agents so as to easily obtain uniform dispersions in water for spraying. For use against soilborne insects, dry granular combinations of insecticides with solid inert carriers may be preferred, according to the common practice in the art.

It is only necessary to apply the insecticide to the zone in which the insects live, or locus of the insects. Normal activity of the insects will assure adequate contact with the insecticide, so that it need not be applied directly to the insects.

I claim:

1. 1-N,N-Dimethylcarbamyl-3-tert.butyl-5-methylthio-1,2,4-triazole.

* * * * *